(12) United States Patent
Schottler

(10) Patent No.: US 8,375,989 B2
(45) Date of Patent: Feb. 19, 2013

(54) METHOD OF OPERATING A CONTROL VALVE ASSEMBLY FOR A HYDRAULIC SYSTEM

(75) Inventor: Chris W. Schottler, Chanhassen, MN (US)

(73) Assignee: Eaton Corporation, Cleveland, OH (US)

( * ) Notice: Subject to any disclaimer, the term of this patent is extended or adjusted under 35 U.S.C. 154(b) by 603 days.

(21) Appl. No.: 12/603,586

(22) Filed: Oct. 22, 2009

(65) Prior Publication Data

US 2011/0094595 A1    Apr. 28, 2011

(51) Int. Cl.
F15B 13/04 (2006.01)
(52) U.S. Cl. .............. 137/596.18; 137/554; 137/625.64; 91/365; 91/367; 91/433; 60/403
(58) Field of Classification Search ............. 137/596.16, 137/596.18, 554, 487.5, 625.64; 91/365, 91/367, 433; 60/403
See application file for complete search history.

(56) References Cited

U.S. PATENT DOCUMENTS

| | | | | |
|---|---|---|---|---|
| 3,437,312 A | * | 4/1969 | Jenney | 137/101.19 |
| 4,143,583 A | * | 3/1979 | Bauer et al. | 91/1 |
| 4,336,745 A | * | 6/1982 | Lund | 91/35 |
| 5,138,838 A | * | 8/1992 | Crosser | 60/433 |
| 5,230,272 A | * | 7/1993 | Schmitz | 91/361 |
| 5,299,420 A | * | 4/1994 | Devier et al. | 60/403 |
| 5,568,759 A | * | 10/1996 | Aardema | 91/461 |
| 5,587,536 A | | 12/1996 | Rasmussen | |
| 5,947,140 A | * | 9/1999 | Aardema et al. | 137/1 |
| 5,960,695 A | * | 10/1999 | Aardema et al. | 91/433 |
| 6,467,264 B1 | * | 10/2002 | Stephenson et al. | 60/460 |
| 7,210,396 B2 | * | 5/2007 | Kuehn et al. | 91/454 |
| 7,353,743 B2 | * | 4/2008 | Bugel et al. | 91/392 |
| 7,475,537 B2 | * | 1/2009 | Spickard | 60/403 |
| 2004/0055453 A1 | * | 3/2004 | Tabor | 91/433 |
| 2005/0051025 A1 | * | 3/2005 | Nielsen et al. | 91/462 |
| 2007/0044465 A1 | | 3/2007 | Zhang et al. | |

FOREIGN PATENT DOCUMENTS

| | | |
|---|---|---|
| DE | 19952591 A1 | 5/2001 |
| EP | 1403525 A1 | 3/2004 |

OTHER PUBLICATIONS

International Search Report for corresponding PCT patent application (PCT/US2010/053691), Feb. 24, 2011 publication date.

* cited by examiner

*Primary Examiner* — John Rivell
*Assistant Examiner* — Matthew W Jellett
(74) *Attorney, Agent, or Firm* — Quinn Law Group, PLLC

(57) ABSTRACT

A method of operating a control valve assembly for a hydraulic system includes detecting the current operation of a first position sensor and a second position sensor to determine if at least one of the first position sensor and the second position sensor is inoperable. A pressure of the fluid at a first work port and a second work port is measured, and one of a first valve and a second valve is actuated when one of the first position sensor and the second position sensor is determined to be inoperable. The first valve is actuated based upon the fluid pressure measured at the second work port to adjust the flow of the fluid through the first work port. The second valve is actuated based upon the fluid pressure measured at the first work port to adjust the flow of the fluid through the second work port.

6 Claims, 2 Drawing Sheets

METHOD OF OPERATING A CONTROL VALVE ASSEMBLY FOR A HYDRAULIC SYSTEM

TECHNICAL FIELD

The invention relates to a method of operating a hydraulic valve assembly for a hydraulic system used to operate an actuator of the hydraulic system.

BACKGROUND OF THE INVENTION

Hydraulic systems for heavy equipment, such as excavators, backhoes, bulldozers, front end loaders, earthmovers, etc., typically include a control valve assembly. The control valve assembly is in fluid communication with and receives a flow of a hydraulic fluid from a pump. The control valve assembly is also in fluid communication with a tank, i.e., a fluid reservoir, and circulates the hydraulic fluid back to the tank. The pump then draws the hydraulic fluid from the tank to circulate to the control valve assembly. The hydraulic valve assembly may include a sub-assembly including a first work port and a second work port, each in fluid communication with an actuator, such as a hydraulic piston or a hydraulic motor. The control valve sub-assembly further includes a first valve configured for controlling a flow of the hydraulic fluid through the first work port, and a second valve configured for controlling a flow of the hydraulic fluid through the second work port. The first valve and the second valve operate to control the flow of the hydraulic fluid to the actuator, to thereby control the movement of the actuator. The control valve assembly typically includes multiple control sub-assemblies for controlling multiple actuators.

The control valve sub-assembly may include a first position sensor configured for sensing a position of the first valve, and a second position sensor configured for sensing a position of the second valve. The first position sensor and the second position sensor provide information feedback to a processor of the sub-assembly, i.e., a sub-assembly computer, on the position of the first and second valves respectively, allowing the processor to adjust the position of the first and second valves to achieve a desired flow based upon the respective positions of the first and second valves, i.e., a position control mode.

The control valve sub-assembly may include a first pressure sensor configured for sensing a fluid pressure of the hydraulic fluid at the first work port, a second pressure sensor for sensing a fluid pressure of the hydraulic fluid at the second work port, a pump pressure sensor configured for sensing a fluid pressure of the hydraulic fluid at the pump, and a tank pressure sensor configured for sensing a fluid pressure of the hydraulic fluid at the tank. The first and second pressure sensors provide information feedback to the sub-assembly processor on the pressure of the hydraulic fluid at the first and second work ports respectively, while the pump pressure sensor and the tank pressure sensor provide information feedback to the sub-assembly processor on the pressure of the hydraulic fluid at the pump and the tank respectively. This information combined with the information on the position of the first and second valves respectively, allows the sub-assembly processor to adjust the position of the first and second valves based upon a flow rate, i.e., a flow control mode. However, failure of one of the position sensors prevents the sub-assembly processor from using the position control mode or the flow control mode to control the first and second valves respectively.

SUMMARY OF THE INVENTION

A method of operating a control valve assembly for a hydraulic system is disclosed. The control valve assembly includes a first work port and a second work port, each in fluid communication with an actuator. The control valve assembly further includes a first valve for controlling a flow of a fluid through the first work port, and a second valve for controlling a flow of the fluid through the second work port. The method includes measuring a pressure of the fluid at the first work port and the second work port; and actuating one of the first valve based upon the fluid pressure measured at the second work port to adjust the flow of the fluid through the first work port, or the second valve based upon the fluid pressure measured at the first work port to adjust the flow of the fluid through the second work port.

In another aspect of the invention, a method of operating a control valve assembly for a hydraulic system is disclosed. The control valve assembly includes a first work port and a second work port, each in fluid communication with an actuator. The control valve assembly further includes a first valve for controlling a flow of a fluid through the first work port, a second valve for controlling a flow of the fluid through the second work port, a first position sensor for sensing a position of the first valve, and a second position sensor for sensing a position of the second valve. The method includes detecting the current operation of the first position sensor and the second position sensor to determine if at least one of the first position sensor and the second position sensor is inoperable; measuring a pressure of the fluid at the first work port and the second work port; and actuating one of the first valve and the second valve when one of the first position sensor and the second position sensor is determined to be inoperable. The first valve is actuated based upon the fluid pressure measured at the second work port to adjust the flow of the fluid through the first work port, and the second valve is actuated based upon the fluid pressure measured at the first work port to adjust the flow of the fluid through the second work port.

Accordingly, the disclosed method enables continued and uninterrupted operation of the control valve assembly when one of the first and second position sensors fails by using the pressure of the hydraulic fluid at the work port associated with the other of the first and second position sensors to control the valve associated with the failed position sensor.

The above features and advantages and other features and advantages of the present invention are readily apparent from the following detailed description of the best modes for carrying out the invention when taken in connection with the accompanying drawings.

DESCRIPTION OF THE PREFERRED EMBODIMENTS

Referring to the Figures, wherein like numerals indicate like parts throughout the several views, a hydraulic system is shown generally at 20. The hydraulic system 20 may be incorporated into a vehicle, such as but not limited to, an excavator, a backhoe, a bulldozer, an earth mover, etc. The hydraulic system 20 includes and controls at least one actuator 22. The actuator 22 may include, but is not limited to, a hydraulic piston or a hydraulic motor. The various components of the hydraulic system 20 and the general function of the various components of the hydraulic system 20 are known within the art. Therefore, the various components of the hydraulic system 20 and the function of each component are only briefly described herein.

Figure 1:
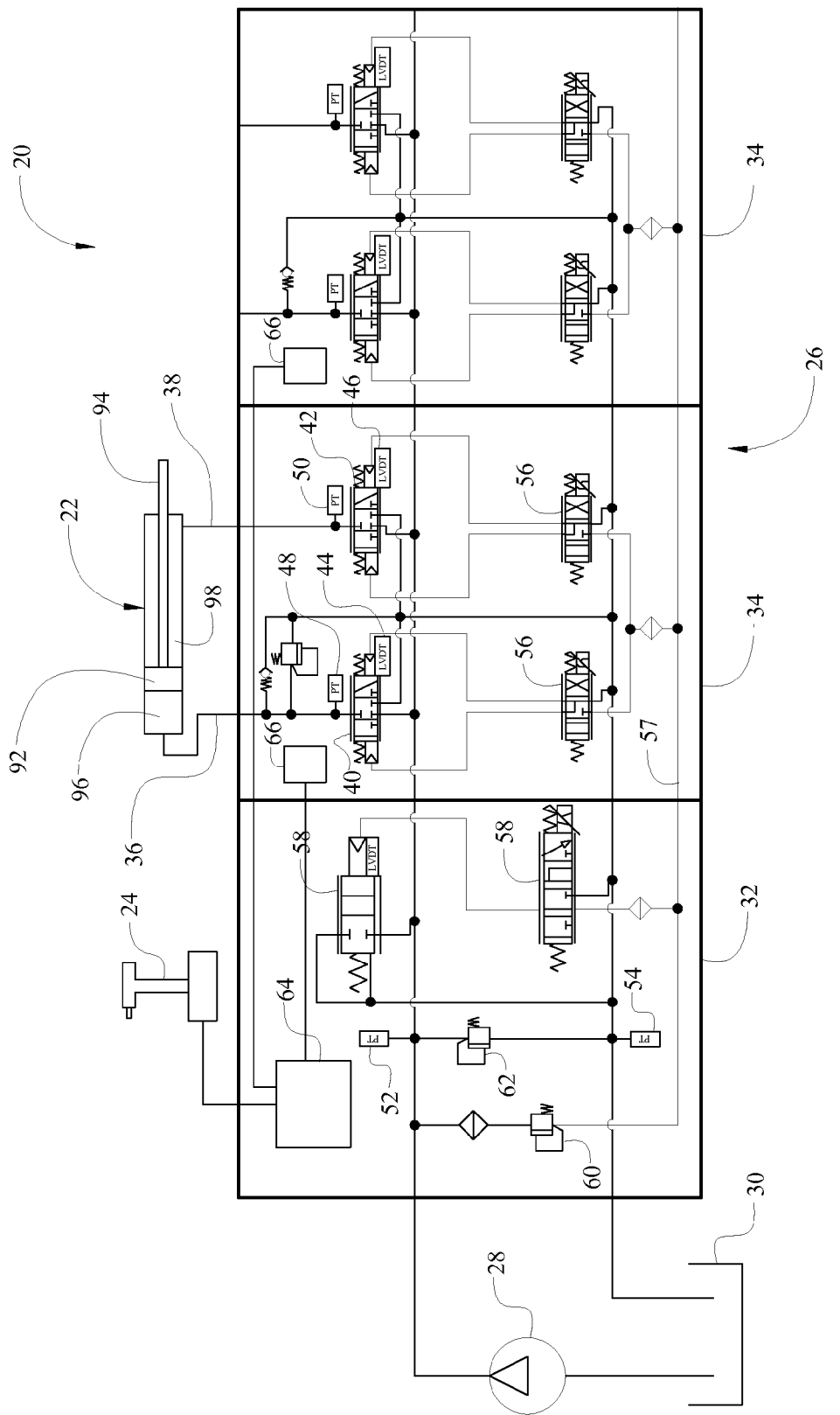
FIG. 1 is a schematic view of a hydraulic system showing a control valve assembly.

Referring to FIG. 1, the hydraulic system 20 includes an input device 24, a control valve assembly 26, a hydraulic pump 28, a tank 30 and the actuator 22. The control valve assembly 26 includes a controller 32 and at least one control valve sub-assembly 34. Typically, the control valve assembly 26 includes a plurality of sub-assemblies 34, with each sub-assembly 34 used to control one actuator 22.

The input device 24 may include a joystick, one or more levers, a touch sensitive screen, or some other device suitable for entering commands into the hydraulic system 20. The input device 24 is coupled to the controller 32 of the control valve assembly 26 to enable an operator to enter commands into the hydraulic system 20.

The hydraulic system 20 includes a fluid, i.e., a hydraulic fluid. The pump 28 pressurizes the hydraulic fluid and provides the pressurized hydraulic fluid to the control valve assembly 26. The control valve assembly 26 supplies the pressurized hydraulic fluid to the sub-assembly 34, which directs the hydraulic fluid to the actuator 22. The control valve assembly 26 is also in fluid communication with the tank 30, which acts as a fluid reservoir for the hydraulic system 20. The pump 28 draws the hydraulic fluid from the tank 30 as needed.

The controller 32 receives the feedback from the input device 24 and the sub-assembly 34, and also directs information from the input device 24 to the sub-assembly 34. The controller 32 may include one or more flow control valves 58, a pilot pressure regulator 60, and a relief pressure regulator 62 to control fluid flow to the sub-assembly 34, as well as, a computer 64 having software, memory, and any other component necessary to provide the sub-assembly 34 with the necessary information to operate and/or control the first valve 40 and the second valve 42. The control valve sub-assembly 34 may further include a sub-assembly processor 66 in communication with the computer 64 of the controller 32. The computer 64 may communicate with the control valve sub-assembly 34 through the processor 66. The processor 66 may include a computer, a memory, software and/or other hardware necessary to communicate with the controller 32 and control the control valve sub-assembly 34. The processor 66 directly controls the pilot valves 56, which in turn control the first valve 40 and the second valve 42, as well as receives the information from the various sensors in the sub-assembly 34 described below.

The control valve sub-assembly 34 includes a first work port 36 and a second work port 38. The first work port 36 is in fluid communication with and configured to supply the hydraulic fluid to the actuator 22. The second work port 38 is also in fluid communication with and configured to supply the hydraulic fluid to the actuator 22. The control valve sub-assembly 34 further includes a first valve 40 and a second valve 42. The first valve 40 is in fluid communication with the pump 28 and the tank 30, and is configured for controlling a flow of the hydraulic fluid through the first work port 36. The second valve 42 is also in fluid communication with the pump 28 and the tank 30, and is configured for controlling a flow of the hydraulic fluid through the second work port 38. The first valve 40 and the second valve 42 may include, but are not limited to, a poppet valve or a spool valve. It should be appreciated that the first valve 40 and the second valve 42 may include any suitable type and/or configuration of valve suitable for controlling pressurized fluid flow through the first work port 36 and the second work port 38 respectively, and may be actuated through electric and/or hydraulic signals. As such, it should be appreciated that the processor 66 signals the pilot valves 56, which control the first valve 40 and the second valve 42 to open and/or close fluid flow through the first work port 36 and the second work port 38 respectively. As shown, the first valve 40 and the second valve 42 include poppet valves controlled via pilot valves 56 of a pilot pressure system 57.

The control valve sub-assembly 34 further includes a first position sensor 44 and a second position sensor 46. The first position sensor 44 is coupled to the first valve 40, and is configured for sensing the position of the first valve 40. The first position sensor 44 is in communication with the processor 66 and provides feedback to the processor 66 on the position of the first valve 40. The second position sensor 46 is coupled to the second valve 42, and is configured for sensing a position of the second valve 42. The second position sensor 46 is in communication with the processor 66 and provides feedback to the processor 66 on the position of the second valve 42.

The control valve sub-assembly 34 further includes a first pressure sensor 48 and a second pressure sensor 50. The first pressure sensor 48 is coupled to and in fluid communication with the first work port 36, and is configured for sensing a fluid pressure of the hydraulic fluid flowing through the first work port 36. The first pressure sensor 48 is in communication with the processor 66 and provides feedback to the processor 66 on the pressure of the hydraulic fluid at the first work port 36. The second pressure sensor 50 is coupled to and in fluid communication with the second work port 38, and is configured for sensing a fluid pressure of the hydraulic fluid flowing through the second work port 38. The second pressure sensor 50 is in communication with the processor 66 and provides feedback to the processor 66 on the pressure of the hydraulic fluid at the second work port 38.

The control valve assembly 26 may further include a pump pressure sensor 52 and a tank pressure sensor 54. A shown, the pump pressure sensor 52 and the tank pressure sensor 54 are disposed in the controller 32. The pump pressure sensor 52 is coupled to and in fluid communication with hydraulic fluid provided from the pump 28, i.e., supply, and is configured for sensing a fluid pressure of the hydraulic fluid at the pump 28, i.e., a supply pressure. The pump pressure sensor 52 is in communication with the computer 64 and provides feedback to the computer 64 on the pressure of the hydraulic fluid at the pump 28. The computer 64 provides the information from the pump pressure sensor 52 to the processor 66. The tank pressure sensor 54 is coupled to and in fluid communication with the hydraulic fluid at the tank 30, and is configured for sensing a fluid pressure of the hydraulic fluid at the tank 30. The tank pressure sensor 54 is in communication with the computer 64 and provides feedback to the computer 64 on the pressure of the hydraulic fluid at the tank 30. The computer 64 provides the information from the tank pressure sensor 54 to the processor 66.

The control valve sub-assembly 34 may operate in either a passive operating condition or an overrunning operating condition. The passive operating condition occurs when a load applied to the actuator 22 resists movement of the actuator 22, i.e., a positive load. The overrunning operating condition occurs when the load applied to the actuator 22 acts in the same direction as movement of the actuator 22, i.e., a negative load. As shown, the actuator 22 includes a piston 92, having a rod 94 extending therefrom. The piston 92 defines a piston end 96 and a rod end 98, with the rod 94 disposed within the rod end 98. Because the rod 94 extends through the rod end 98, the surface area of the piston 92 at the rod end 98 on which the hydraulic fluid acts is less than the surface area of the piston 92 at the piston end 96 on which the hydraulic fluid acts. The ratio of the surface area on the piston end 96 of the piston 92 relative to the rod end 98 of the piston 92 defines an area ratio of the actuator 22. The area ratio of the actuator 22 affects both the fluid flow rate through the first work port 36 and the second work port 38, as well as the fluid pressure at the first work port 36 and the second work port 38. Accordingly, the area ratio of the actuator 22 must be considered in determining whether the control valve sub-assembly 34 is operating in the passive operating condition or the overrunning operating condition.

Additionally, one of the first work port 36 and the second work port 38 operates as an upstream work port, while the other of the first work port 36 and the second work port 38 operates as a downstream work port. Which of the first work port 36 and the second work port 38 is the upstream work port and the downstream work port depends upon the direction of the flow of the hydraulic fluid, and therefore changes during operation of the hydraulic system 20. Accordingly, it should be appreciated that one of the first work port 36 and the second work port 38 is associated with the upstream work port, and the other of the first work port 36 and the second work port 38 is associated with the downstream work port. It should also be appreciated that the upstream work port is also associated with the valve, the position sensor and the pressure sensor corresponding to the specific work port currently defined as the upstream work port. Similarly, it should be appreciated that the downstream work port is also associated with the valve, the position sensor and the pressure sensor corresponding to the specific work port currently defined as the downstream work port. The upstream work port is the work port that is currently controlling the flow of the hydraulic fluid provided to the actuator 22. The downstream work port is the work port that is currently controlling the flow of the hydraulic fluid received from the actuator 22. Accordingly, the first work port 36 and the second work port 38 may be operating in one of the following conditions: as the upstream work port in the passive operating condition, as the upstream work port in the overrunning operating condition, as the downstream work port in the passive operating condition, or as the downstream work port in the overrunning operating condition.

Under normal operating conditions, the processor 66 may control the first valve 40 and the second valve 42 using one of a flow control mode, a pressure control mode, or a position control mode. Which of the flow control mode, the pressure control mode and the position control mode the processor 66 utilizes to control one of the first work port 36 and the second work port 38 typically depends upon whether that specific work port is operating as the upstream work port in the passive operating condition, as the upstream work port in the overrunning operating condition, as the downstream work port in the passive operating condition, or as the downstream work port in the overrunning operating condition.

When controlling the first valve 40 by the flow control method, the processor 66 uses a demand received from the input device 24, feedback from the first pressure sensor 48 relating to the fluid pressure of the hydraulic fluid at the first work port 36, feedback from the pump pressure sensor 52 relating to the fluid pressure at the pump 28, i.e., the supply pressure, and feedback from the tank pressure sensor 54 relating to the fluid pressure at the tank 30. The processor 66 uses the demand and the various feedbacks to control a position of the first valve 40, which results in meeting the desired demand. Similarly, when controlling the second valve 42 by the flow control method, the processor 66 uses the demand received from the input device 24, feedback from the second pressure sensor 50 relating to the fluid pressure of the hydraulic fluid at the second work port 38, feedback from the pump pressure sensor 52 relating to the fluid pressure at the pump 28, i.e., the supply pressure, and feedback from the tank pressure sensor 54 relating to the fluid pressure at the tank 30. The processor 66 uses the demand and the various feedbacks to control a position of the second valve 42, which results in meeting the desired demand.

When controlling the first valve 40 by the pressure control method, the processor 66 moves the first valve 40 as necessary to achieve a desired fluid pressure at the first work port 36. The processor 66 receives feedback from the first pressure sensor 48 related to the fluid pressure of the hydraulic fluid at the first work port 36, and adjusts the position of the first valve 40 accordingly to achieve the desired fluid pressure at the first work port 36. When controlling the second valve 42 by the pressure control method, the processor moves the second valve 42 as necessary to achieve a desired fluid pressure at the second work port 38. The processor 66 receives feedback from the second pressure sensor 50 related to the fluid pressure of the hydraulic fluid at the second work port 38, and adjusts the position of the second valve 42 accordingly to achieve the desired fluid pressure at the second work port 38.

When controlling the first valve 40 by the position control mode, the processor 66 uses feedback from the first position sensor 44 to determine the current position of the first valve 40. The processor 66 calculates a required position necessary to achieve the desired fluid flow through the first work port 36. The processor 66 then moves the first valve 40 into the required position to throttle the flow of the hydraulic fluid through the first work port 36. When controlling the second valve 42 by the position control mode, the processor 66 uses feedback from the second position sensor 46 to determine the current position of the second valve 42. The processor 66 calculates a required position necessary to achieve the desired fluid flow through the second work port 38. The processor 66 then moves the second valve 42 into the required position to throttle the flow of the hydraulic fluid through the second work port 38. Accordingly, it should be appreciated that failure of one of the first position sensor 44 and the second position sensor 46 renders the flow control mode and the position control mode inoperable for the first control valve and the second control valve respectively.

Accordingly, the invention provides a method of controlling the control valve sub-assembly 34 when one of the first position sensor 44 and the second position sensor 46 has failed, i.e., is inoperable. As used herein, the term "inoperable" is defined as being present but not capable of operating as intended for any reason. The method is dependent upon whether the failed position sensor is associated with, and configured for sensing the position of the valve associated with, the upstream work port or the downstream work port, and whether the control valve sub-assembly 34 is operating in the passive operating condition or the overrunning operating condition. As such, each possible variation is described in detail below. As noted above, either the first work port 36 or the second work port 38 may be defined as the upstream work port or the downstream work port. Therefore, the below described method is applicable to both the first work port 36 and the second work port 38.

The following describes the method when the failed position sensor is associated with the upstream work port, and is operating in the passive operating condition. The method of operating the valve associated with the upstream work port in this situation includes using feedback from the pressure sensor associated with the downstream work port to control the pressure associated with the upstream work port, referred to as cross axis pressure control. When using cross axis pressure control in this situation, the position of the valve associated with the upstream work port and the failed position sensor is controlled to achieve a set fluid pressure of the hydraulic fluid at the downstream work port. The processor 66 actuates the valve associated with and configured for controlling the upstream work port to achieve the required downstream fluid pressure in the hydraulic fluid flowing through the downstream work port. Because the position sensor associated with the valve controlling fluid flow through the downstream work port is still functioning properly in this situation, the processor 66 preferably operates the valve associated with and configured for controlling the downstream work port in the flow control mode as described above.

The following describes the method when the failed position sensor is associated with the upstream work port, and is operating in the overrunning operating condition. The method of operating the valve associated with the upstream work port in this situation includes using the pressure control method described above to control the valve associated with and configured for controlling the flow of the hydraulic fluid through the upstream work port. Accordingly, the processor 66 actuates the valve associated with the upstream work port to maintain a desired fluid pressure at the upstream work port. Alternatively, the valve associated with the upstream work port in this situation may be fully opened to tank 30, essentially eliminating restrictions in the flow between the actuator 22 and the tank 30. Because the position sensor associated with the valve controlling fluid flow through the downstream work port is still functioning properly in this situation, the processor 66 preferably operates the valve associated with and configured for controlling the downstream work port in the flow control mode as described above.

The following describes the method when the failed position sensor is associated with the downstream work port, and is operating in the passive operating condition. Because the failed position sensor is associated with the valve controlling the downstream work port, i.e., the work port controlling flow out of the actuator 22, the valve associated with the downstream work port merely needs to control the pressure of the hydraulic fluid at the downstream work port to be slightly more than the pressure of the hydraulic fluid at the tank port. Accordingly, the method of operating the valve associated with the downstream work port in this situation includes using feedback from the pressure sensor associated with the downstream work port to control the valve associated with and configured for controlling the flow of the hydraulic fluid through the downstream work port, i.e., the pressure control mode described above. Because the position sensor associated with the valve controlling fluid flow through the upstream work port is still functioning properly in this situation, the processor 66 preferably operates the valve associated with and configured for controlling the upstream work port in the flow control mode as described above.

The following describes the method when the failed position sensor is associated with the downstream work port, and is operating in the overrunning operating condition. Because the upstream work port controls the flow of the hydraulic fluid to the actuator 22, and the control valve assembly 26 is operating in the overrunning operating condition, the valve controlling the flow of the hydraulic fluid through the downstream work port need only restrict the flow of the hydraulic fluid sufficiently to prevent cavitation in the hydraulic fluid. Accordingly, the method of operating the valve associated with the downstream work port in this situation includes using feedback from the pressure sensor associated with the upstream work port to control the valve associated with and configured for controlling the flow of the hydraulic fluid through the downstream work port, i.e., cross axis pressure control. When using cross axis pressure control in this situation, the position of the valve associated with the downstream work port and the failed position sensor is controlled to achieve a set fluid pressure of the hydraulic fluid at the upstream work port. The processor 66 actuates the valve associated with and configured for controlling the downstream work port to achieve the required upstream fluid pressure in the hydraulic fluid flowing through the upstream work port. Because the position sensor associated with the valve controlling fluid flow through the upstream work port is still functioning properly in this situation, the processor 66 preferably operates the valve associated with and configured for controlling the upstream work port in the flow control mode as described above.

Figure 2:
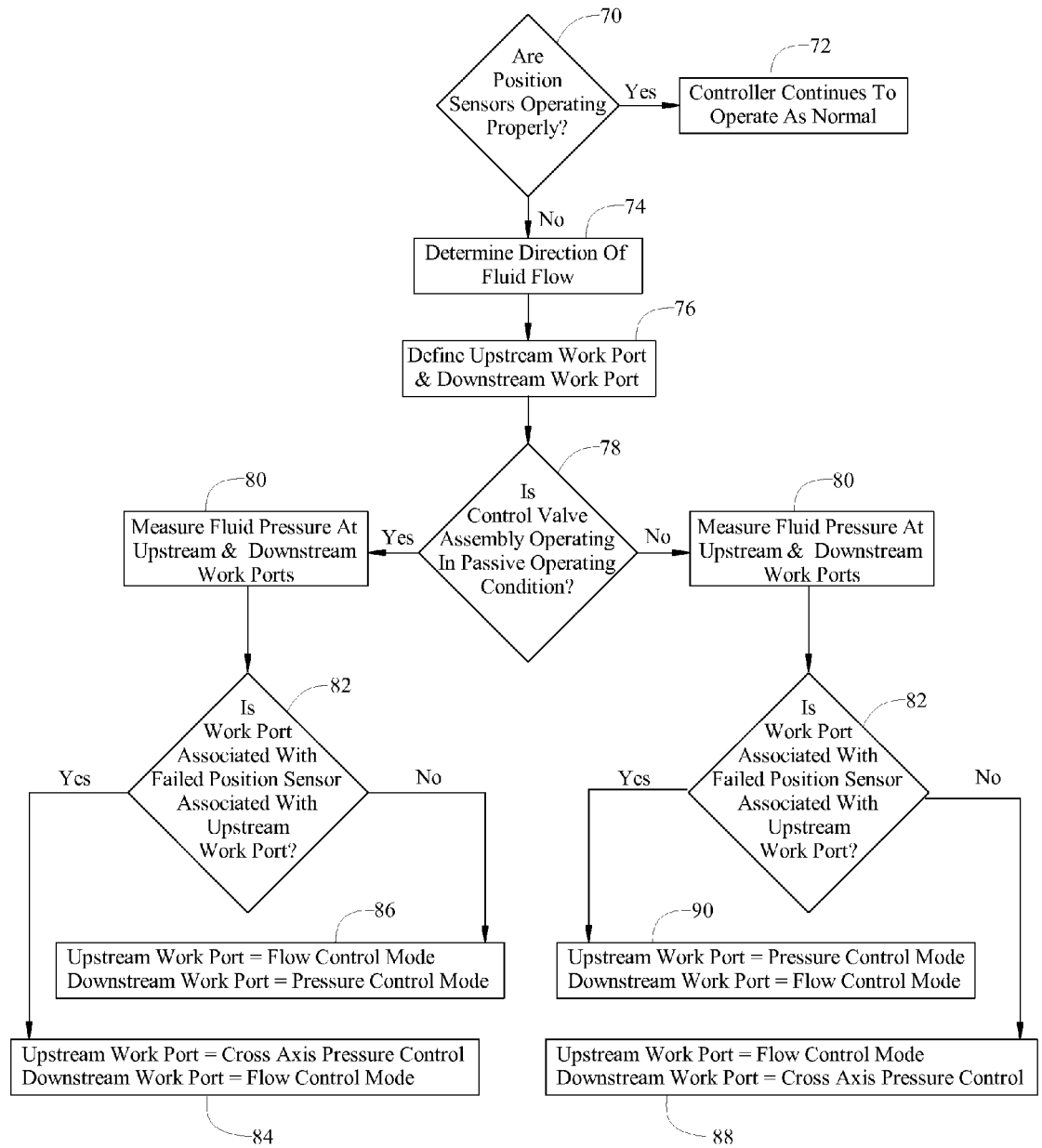
FIG. 2 is a flow chart of a method of operating the control valve assembly.

Referring to FIG. 2, the method of controlling the control valve assembly 26 includes detecting the current operation of the first position sensor 44 and the second position sensor 46 to determine if at least one of the first position sensor 44 and the second position sensor 46 is inoperable. The processor 66 may determine whether the first position sensor 44 or the second position sensor 46 is operable in any suitable manner known to those skilled in the art, such as detecting the presence of a feedback signal from the first position sensor 44 and the second position sensor 46.

If both the first position sensor 44 and the second position sensor 46 are properly functioning (block 70), then the processor 66 continues to operate the control valve sub-assembly 34 as normal (block 72). If however, one of the first position sensor 44 or the second position sensor 46 is determined to be inoperable (block 70), then the method further includes determining the direction of fluid flow (block 74) through each of the first work port 36 and the second work port 38 to define one of the first work port 36 and the second work port 38 as the upstream work port and define the other of the first work port 36 and the second work port 38 as the downstream work port (block 76). The method further includes determining an operating condition of the control valve assembly 26 to be one of a passive condition and an overrunning condition (block 78). As described above, the manner in which the processor 66 manipulates the control valve sub-assembly 34 is dependent upon whether the failed position sensor is associated with the upstream work port or the downstream work port, and whether the control valve sub-assembly 34 is operating in the passive operating condition or the overrunning operating condition.

The method further includes measuring a pressure of the fluid at the first work port 36 and the second work port 38 (block 80). As described above, the pressure of the hydraulic fluid is measured at the first work port 36 and the second work port 38 by the first pressure sensor 48 and the second pressure sensor 50 respectively. The first pressure sensor 48 and the second pressure sensor 50 provide a feedback signal to the processor 66 indicating the current pressure of the hydraulic fluid.

The method further includes determining whether the failed position sensor is associated with the valve controlling the upstream work port or the valve controlling the downstream work port (block 82).

The method further includes actuating one of the first valve 40, based upon the fluid pressure measured at the second work port 38 to adjust the flow of the fluid through the first work port 36, or the second valve 42, based upon the fluid pressure measured at the first work port 36 to adjust the flow of the fluid through the second work port 38. Actuating one of the first valve 40 or the second valve 42 may further include actuating one of the first valve 40 to adjust the flow of the fluid through the work port to within a range of the fluid pressure measured at the second work port 38, or the second valve 42 to adjust the flow of the fluid through the work port to within a range of the fluid pressure measured at the first port, wherein the range includes a positive value between 0 bars and 20 bars. Adjusting the valve associated with the failed position sensor to achieve a fluid pressure to within the range of the fluid pressure measured at the other work port ensures that the fluid pressure at the work port associated with the failed position valve is greater than the fluid pressure associated with the other work port.

Actuating one of the first valve 40 and the second valve 42 may further include actuating the one of the first valve 40 and the second valve 42 associated with the upstream work port based upon the measured pressure at the downstream work port when the control valve assembly 26 is operating in the passive operating condition and the one of the first position sensor 44 and the second position sensor 46 associated with the upstream work port is inoperable (block 84). Accordingly, the processor 66 uses the flow control mode to control the valve associated with the upstream work port, and uses cross axis pressure control to control the valve associated with the downstream work port. In this situation, the method may further include calculating a fluid flow demand for the downstream work port, calculating a required fluid flow rate for the downstream work port sufficient to meet the calculated fluid flow demand, and adjusting the one of the first valve 40 and the second valve 42 associated with the downstream work port to satisfy the calculated fluid flow rate.

If the work port associated with the failed position sensor is associated with the downstream work port and the control valve sub-assembly 34 is operating in the passive operating condition, then the controller 32 uses the flow control mode to control the valve associated with the upstream work port and the pressure control mode to control the valve associated with the downstream work port (block 86).

Actuating one of the first valve 40 and the second valve 42 may further include actuating the one of the first valve 40 and the second valve 42 associated with the downstream work port based upon the measured pressure at the upstream work port when the control valve assembly 26 is operating in the overrunning operating condition and the one of the first position sensor 44 and the second position sensor 46 associated with the downstream work port is inoperable (block 88). Accordingly, the controller 32 uses the flow control mode to control the valve associated with the upstream work port and uses cross axis pressure control to control the valve associated with the downstream work port. In this situation, the method may further include setting a fluid flow demand for the upstream work port, calculating a required fluid flow rate for the upstream work port sufficient to meet the set fluid flow demand, and adjusting one of the first valve 40 and the second valve 42 associated with the upstream work port to satisfy the calculated fluid flow rate.

If the work port associated with the failed position sensor is associated with the upstream work port and the control valve sub-assembly 34 is operating in the overrunning operating condition, then the controller 32 uses the pressure control mode to control the valve associated with the upstream work port and the flow control mode to control the vale associated with the downstream work port (block 90).

While the best modes for carrying out the invention have been described in detail, those familiar with the art to which this invention relates will recognize various alternative designs and embodiments for practicing the invention within the scope of the appended claims.

The invention claimed is:

1. A method of operating a control valve assembly for a hydraulic system, the control valve assembly including a first work port and a second work port each in fluid communication with an actuator, a first valve associated with the first work port for controlling a flow of a fluid through the first work port, a second valve associated with the second work port for controlling a flow of the fluid through the second work port, a first position sensor associated with the first valve for sensing a position of the first valve, and a second position sensor associated with the second valve for sensing a position of the second valve, the method comprising:

detecting the current operation of the first position sensor and the second position sensor to determine if both the first position sensor and the second position sensor are operable, or if at least one of the first position sensor and the second position sensor is inoperable;

controlling a position of the first valve and a position of the second valve based upon a position of the first valve and the second valve sensed by the first position sensor and the second position sensor respectively when both the first position sensor and the second position sensor are determined to be operable;

determining an operating condition of the control valve assembly to be one of a passive condition or an overrunning condition;

defining one of the first work port and the second work port as an upstream work port, and defining the other of the first work port and the second work port as a downstream work port;

measuring a pressure of the fluid at the first work port and the second work port;

actuating the one of the first valve and the second valve controlling fluid flow through the upstream work port based upon the fluid pressure measured at the downstream work port to adjust the flow of the fluid through the upstream work port when the control valve assembly is determined to be operating in the passive condition and the position sensor associated with the one of the first valve and the second valve controlling fluid flow through the upstream work port is determined to be inoperable;

actuating the one of the first valve and the second valve associated with the downstream work port based upon a position of the one of the first valve and the second valve controlling fluid flow through the downstream work port sensed by the position sensor associated with the one of the first valve and the second valve controlling fluid flow through the downstream work port when the control valve assembly is determined to be operating in the passive condition and the position sensor associated with the one of the first valve and the second valve controlling fluid flow through the upstream work port is determined to be inoperable;

actuating the one of the first valve and the second valve controlling fluid flow through the downstream work port based upon the fluid pressure measured at the upstream work port to adjust the flow of the fluid through the downstream work port when the control valve assembly is determined to be operating in the overrunning condition and the position sensor associated with the one of the first valve and the second valve controlling fluid flow through the downstream work port is determined to be inoperable; and actuating the one of the first valve and the second valve associated with the upstream work port based upon a position of the one of the first valve and the second valve controlling fluid flow through the upstream work port sensed by the position sensor associated with the one of the first valve and the second valve controlling fluid flow through the upstream work port when the control valve assembly is determined to be operating in the overrunning condition and the position sensor associated with the one of the first valve and the second valve controlling fluid flow through the downstream work port is determined to be inoperable.

2. A method as set forth in claim 1 wherein actuating the one of the first valve and the second valve controlling fluid flow through the upstream work port based upon the fluid pressure measured at the downstream work port is further defined as actuating the one of the first valve and the second valve controlling fluid flow through the upstream work port based upon the fluid pressure measured at the downstream work port to adjust the flow of the fluid through the upstream work port to within a range of the fluid pressure measured at the downstream work port, and wherein actuating the one of the first valve and the second valve controlling fluid flow through the downstream work port based upon the fluid pressure measured at the upstream work port is further defined as actuating the one of the first valve and the second valve controlling fluid flow through the downstream work port based upon the fluid pressure measured at the upstream work port to adjust the flow of the fluid through the downstream work port to within a range of the fluid pressure measured at the upstream work port.

3. A method as set forth in claim 1 further comprising calculating a fluid flow demand for the downstream work port.

4. A method as set forth in claim 3 further comprising adjusting one of the first valve and the second valve associated with the downstream work port to satisfy the calculated fluid flow demand.

5. A method as set forth in claim 1 further comprising setting a fluid flow demand for the upstream work port.

6. A method as set forth in claim 5 further comprising adjusting one of the first valve and the second valve associated with the upstream work port to satisfy the calculated fluid flow demand.

* * * * *